United States Patent [19]

Tsay et al.

[11] Patent Number: 5,089,387

[45] Date of Patent: * Feb. 18, 1992

[54] DNA PROBE DIFFRACTION ASSAY AND REAGENTS

[75] Inventors: Yuh-Geng Tsay, San Jose; Emanuel Calenoff; Eric K. Gustafson, both of Palo Alto; Rick Trebino, Livermore; John Lee, Cupertino, all of Calif.

[73] Assignee: Adeza Biomedical Corporation, Sunnyvale, Calif.

[*] Notice: The portion of the term of this patent subsequent to Dec. 12, 2006 has been disclaimed.

[21] Appl. No.: 216,691

[22] Filed: Jul. 7, 1988

[51] Int. Cl.$^5$ .......................... G01N 33/543
[52] U.S. Cl. .......................... 435/6; 422/55; 436/518; 436/524; 436/531
[58] Field of Search .......................... 422/55; 436/518, 524, 436/531; 435/6; 424/250

[56] References Cited

U.S. PATENT DOCUMENTS

| | | | |
|---|---|---|---|
| 3,853,467 | 1/1974 | Giaever | 23/230 |
| 3,926,564 | 7/1975 | Giaever | 23/259 |
| 3,960,451 | 4/1976 | Wirz et al. | 356/161 |
| 3,960,488 | 7/1976 | Giaever | 23/230 |
| 3,960,489 | 11/1976 | Giaever | 23/230 |

(List continued on next page.)

FOREIGN PATENT DOCUMENTS 0167335 10/1986 European Pat. Off.
86308568 11/1986 European Pat. Off.
PCT/GB85/-
00427 9/1985 PCT Int'l Appl.

OTHER PUBLICATIONS

Arwin, H., et al., "A Reflectance Method of Immunological Reactions on Surfaces", *Analyt. Biochem.* 145:106-112 (1985).

Moffatt, A., "Optical Probes May Hasten Shift of Diagnostics from Lab to Doc's Office", *Gen. Eng. News* p. 18, Oct. 1986.

Pace, S., "Biosensors and the Clinical Laboratory", *Med. Inst.* 19:168-172 (1985).

Grunstein, et al., *Proc. Natl. Acad. Sci., U.S.A.* 72:3961-3965 (1975).

*Primary Examiner*—Amelia Burgess Yarbrough
*Assistant Examiner*—Jeffrey Stucker
*Attorney, Agent, or Firm*—Skjerven, Morrill, MacPherson, Franklin & Friel

[57] ABSTRACT

The assay of the subject invention uses DNA sequences as probes in a nucleic acid hybridization diffraction assay, to detect specific DNA sequences in a sample. Diffraction assay methodologies are applied to determine the presence and amount of analyte.

This invention involves a discovery in the areas of supporting surfaces for a biogrid or biograting which provide greatly reduced non-specific hybridization and binding. A preferred process of this invention involves manufacturing a biograting for use in a light diffraction assay, and comprises adhering a uniform layer of hybridizing reagent comprising a nucleotide sequence on a smooth, solid surface and exposing the surface to UV radiation through a shadow mask with a diffraction grating pattern of lines to selectively deactivate the hybridizing reagent, leaving a biological diffraction grating design of lines of active hybridizing reagent. The smooth, solid surface is preferably selected from the group consisting of polysilicon and single crystalline silicon surfaces.

The diffraction hybridizing assay method of this invention for determining the presence or quantity of an analyte in an aqueous sample comprises contacting a nucleic acid sequence diffraction biogrid with the sample under proper circumstances and for a sufficient time to permit nucleic acid hybridization between a nucleic acid sequence probe and an analyte; separating the biogrid from the sample; illuminating the biogrid with light from a light source; and determining the light diffracted by the diffraction hybridization assay surface.

20 Claims, 3 Drawing Sheets

U.S. PATENT DOCUMENTS

| | | | |
|---|---|---|---|
| 3,960,490 | 9/1976 | Giaever | 23/230 B |
| 3,975,238 | 3/1976 | Bean et al. | 195/103.5 R |
| 3,979,184 | 1/1976 | Giaever | 23/253 |
| 3,979,509 | 11/1976 | Giaever | 424/12 |
| 4,011,308 | 5/1977 | Giaever | 424/1.5 |
| 4,018,886 | 6/1977 | Giaever | 424/12 |
| 4,054,646 | 12/1977 | Giaever | 424/12 |
| 4,115,535 | 10/1978 | Giaever | 424/1 |
| 4,172,827 | 1/1979 | Giaever | 260/112 |
| 4,181,501 | 7/1980 | Keese et al. | 23/230 |
| 4,487,839 | 4/1984 | Kamentsky | 436/518 |
| 4,521,522 | 11/1985 | Lundstrom et al. | 436/525 |
| 4,537,861 | 2/1985 | Elings et al. | 436/518 |
| 4,563,417 | 1/1986 | Albarella | 435/6 |
| 4,647,544 | 9/1987 | Nicoli et al. | 436/518 |
| 4,689,295 | 8/1987 | Taber | 435/6 |

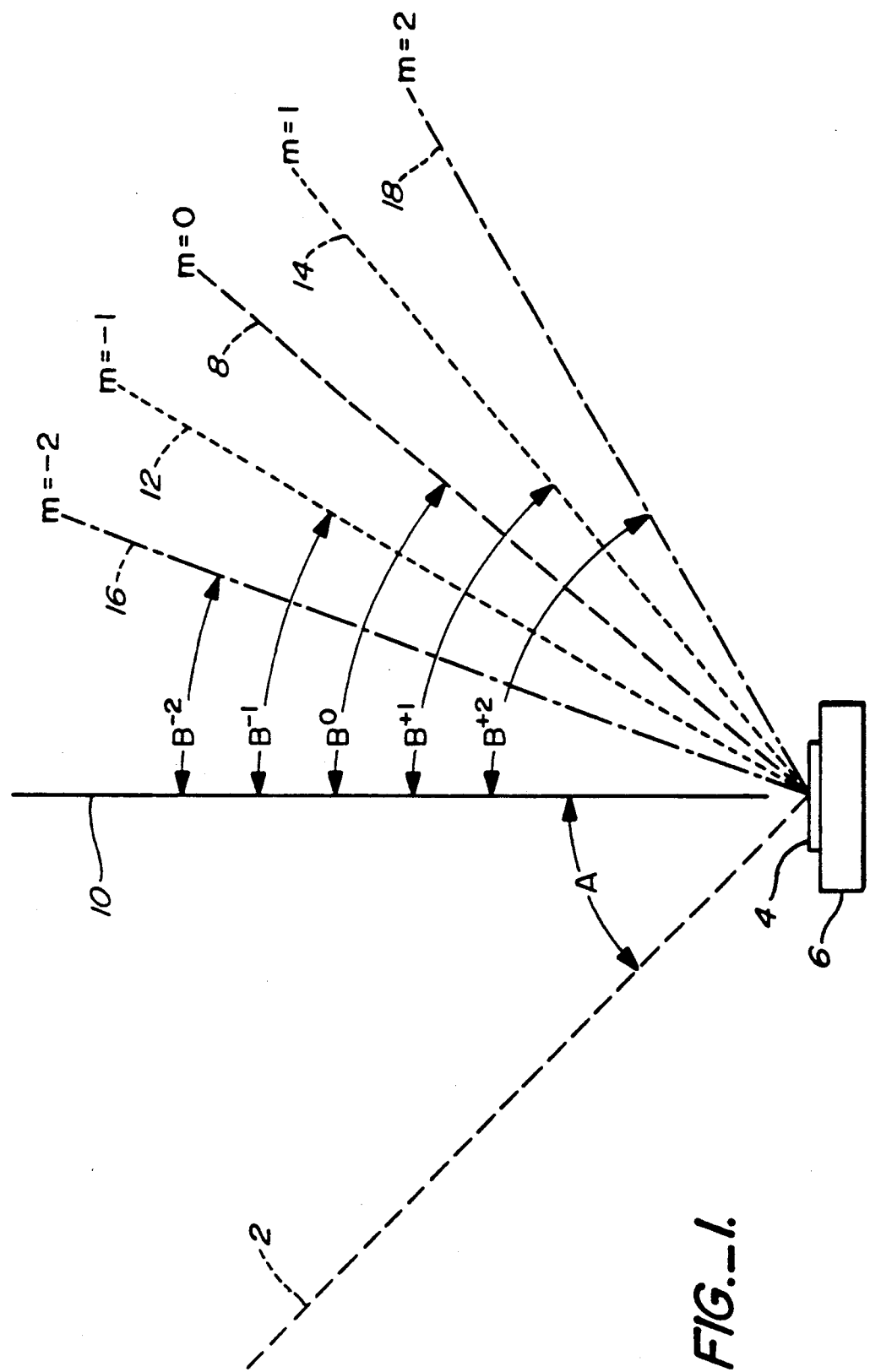
FIG._1.

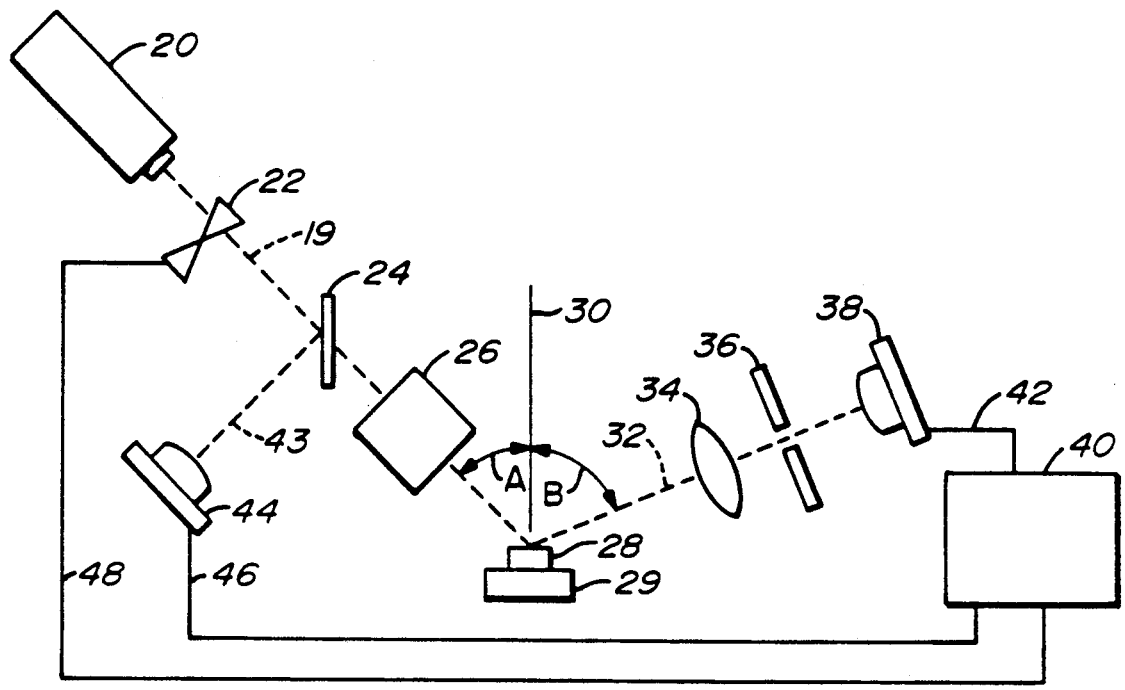
FIG._2.
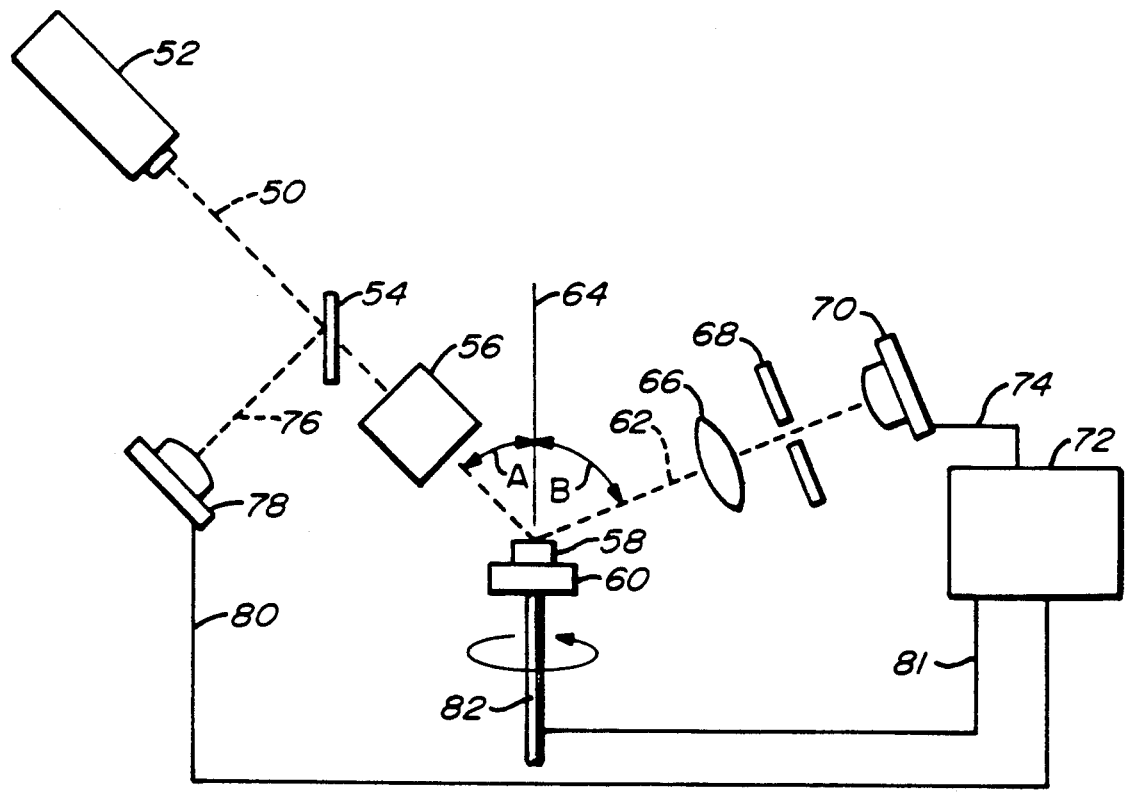
FIG._3.

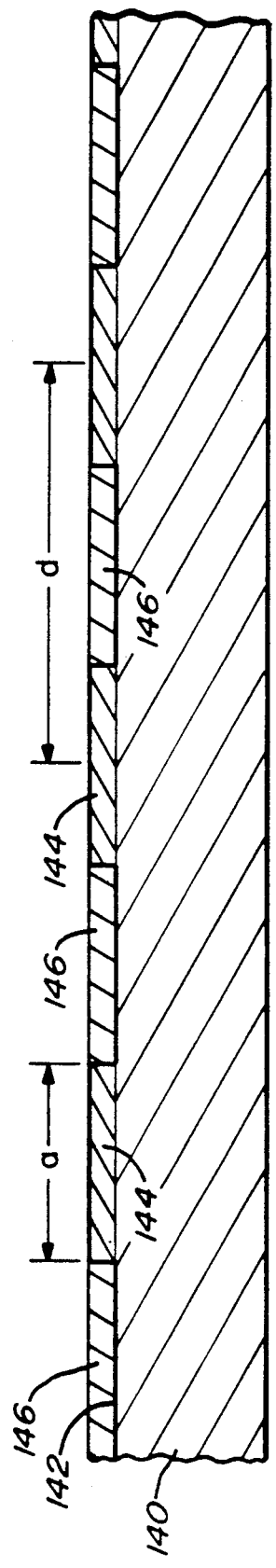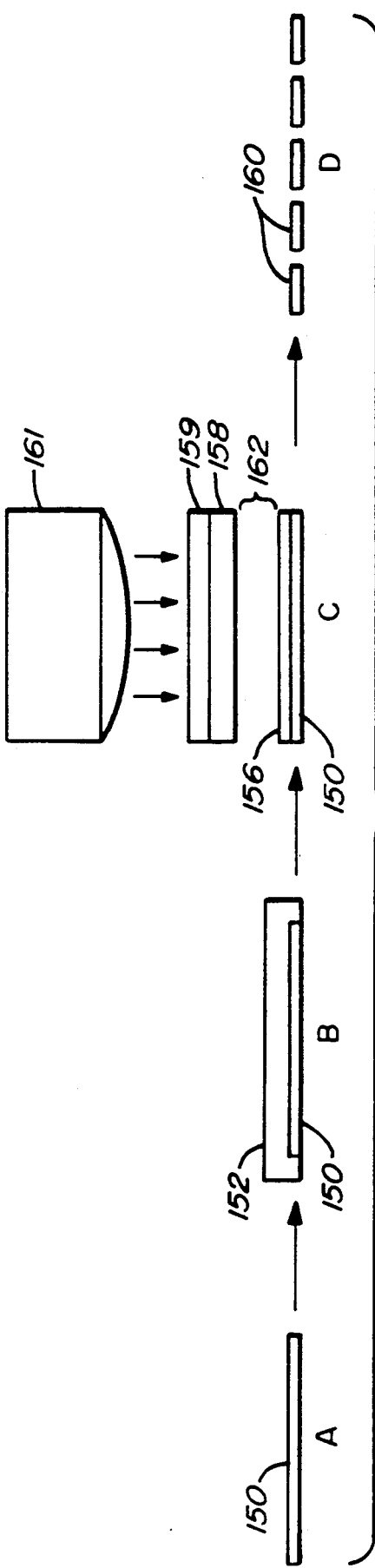

DNA PROBE DIFFRACTION ASSAY AND REAGENTS

RELATIONSHIP TO COPENDING APPLICATIONS

This application is a continuation-in-part of copending U.S. applications Ser. No. 9,177 filed Jan. 30, 1987, now Pat. No. 4,876,208; Ser. No. 30,327 filed Mar. 26, 1987, now Pat. No. 4,886,761; and Ser. No. 34,876 filed Apr. 6, 1987, abandoned.

FIELD OF THE INVENTION

This invention relates to an improved assay method and reagents therefor. In particular this invention relates to a light diffraction assay method using DNA sequences as probes, and reagents which provide enhanced sensitivity.

BACKGROUND OF THE INVENTION

Many solid-phase immunoassays involve surface illumination and consequent light emissions from molecules attached to the surface. Generally, these emissions travel in all directions. Either these divergent emissions must be collected with expensive and awkward light collection optics to achieve sensitivity or the inherent inefficiencies and consequent low signal to light level ratios must be accepted.

Diffraction gratings cause light to be diffracted into specific angles as contrasted to being scattered in all directions. The original gratings were prepared by ruling a number of straight, parallel grooves in a surface. Incident light is diffracted by each of the surfaces and is principally directed in directions in which light from each groove interferes constructively with light scattered by the other grooves. This constructive light interference property of a grating allows efficient collection of light. Diffraction gratings have been used for dispersing light into its spectral components.

Many assay systems have been developed using different physically measurable properties of reagents to provide a measurement of an analyte concentration in a sample. Radioimmunoassay (RIA), immunofluorescence, chemiluminescence, enzyme immunoassays (EIA), free radical immunoassays (FRAT), light scattering nephelometry, transistor bridge probes, indium reflective surfaces, and ultrasonic probes have been applied. These systems use the highly selective reaction between a primary binding reagent material such as an antibody or antigen and an analyte selectively binding therewith. Due to limits of sensitivity, however, prior art systems have required the use of relatively large analytes, such as antibodies or large antigens, or require the use of sandwich assay techniques to increase the detectable signal.

DESCRIPTION OF THE PRIOR ART

U.S. Pat. No. 4,647,544 corresponding to European Patent application 85304496.4 published Jan. 8, 1986 describes a light diffraction system and method, and biogratings therefor, the entire contents of which are hereby incorporated by reference in their entireties. Disclosed methods for forming the biogratings comprise forming a coating of an active antibody on a flat surface such as a glass or plastic surface. In one disclosed method, the selective destruction of antibody molecules to form stripe-like regions is accomplished with an intense UV source such as a mercury lamp together with a shadow mask placed near or in contact with the coated surface. Binding of analytes with the stripes of active antibody yields a light-diffracting grating. In the sandwich assay and competition assay applications of this technology, a labeled reagent ligand can be used to enhance the mass of a bound material.

Photoresists and laser light have been used to make holographic gratings. The coarseness of the photographic medium restricts the groove spacing. Use of photoresist masks in the production of precisely configured shapes and lines in semiconductor material is widely used in the production of semiconductor devices. The masks can be placed on or very near the surface to be exposed as described in U.S. Pat. No. 4,647,544. In this approach, the best line definition is obtained by pressing the mask against the surface to be exposed with high pressure to minimize light reflection at the edges of the masking elements.

U S. Pat. No. 4,521,522, issued to Lundstrom, et al., presents a method for determining antigen-antibody binding using reflected electromagnetic radiation.

The biogrids and biogratings of the prior art have been limited by the resolution of the systems used. The biogratings have generally been limited to assays involving determination of antibodies or relatively large antigens, or the use of sandwich assays.

The analysis and detection of minute quantities of substances in biological samples has become a routine practice in clinical and analytical laboratories. DNA probes are used in a technique based on nucleic acid hybridization (polynucleotide sequence-based techniques). These are characterized by a sequence of steps comprising the non-covalent hybridizing of a labeled polynucleotide sequence or probe to a complementary sequence of the analyte under hybridization conditions. Such procedures are described by M. Grunstein, et al., PNAS, USA 72:3961-3965 (1975).

DNA hybridizations have taken place in situ, i.e., within tissue samples, or in vitro, i.e., with substances which have been separated from tissue. This invention relates to such in vitro DNA hybridizations, and improved detection thereof.

It is desirable to detect when hybridization takes place between the reagent polynucleotide sequence and the complementary sequence of the analyte. This detection has been effected in the prior art by using labeled probe sequences. The test sample is bound to a support, and labeled probe is contacted thereto. Sufficient time is allowed for hybridization, and excess probe is removed. The presence and amount of label present in the sample corresponds to the presence and amount of the analyte. Alternatively, the DNA probe may act as a primary binding agent in a sandwich assay, and a labeled second binding partner for the probe is used to amplify the signal. Common labels include radiolabels, enzyme labeling, and immunofluorescent or chemiluminescent labels.

Exemplary DNA assays are described in U.S. Pat. No. 4,563,417, which describes a nucleic acid hybridization assay using antibodies to intercalation complexes, and in U.S. Pat. No. 4,689,295, which describes a DNA probe test for salmonella.

SUMMARY OF THE INVENTION

The improved assay of the subject invention uses DNA sequences as probes in a nucleic acid hybridization diffraction assay to detect specific DNA sequences in a sample. Diffraction assay methodologies are applied to determine the presence and amount of analyte.

This invention involves a discovery in the area of supporting surfaces for the biogrid or biograting which provide greatly reduced non-specific hybridization or binding. A preferred process of this invention involves manufacturing a biograting for use in a light diffraction assay, and comprises adhering a uniform layer of hybridizing reagent comprising a nucleotide sequence on a smooth, solid surface and exposing the surface to UV radiation through a shadow mask with diffraction grating pattern of lines to selectively deactivate the hybridizing reagent, leaving a biological diffraction grating design of lines of active hybridizing reagent. The smooth, solid surface is a semiconductor, preferably selected from the group consisting of polysilicon and single crystalline silicon surfaces. By use of the process, the sensitivity of the biogrid is improved such that a nucleotide sequence may be applied to a biogrid surface, and the biogrid used in a nucleic acid hybridization assay.

Another preferred biograting of this invention for use in a light diffraction assay comprises a surface preferably selected from the group consisting of polysilicon and single crystalline silicon surfaces having on said surface, a biological diffraction grating design of lines of active hybridizing reagent which is the product of the process of adhering a uniform layer of a nucleic acid sequence on a smooth, solid surface and exposing the surface to UV radiation through a shadow mask with diffraction grating pattern lines to selectively deactivate the hybridizing reagent nucleic acid sequence to leave a biological diffraction grating design of lines of active nucleic acid sequence, wherein a precise focused shadow is cast on the nucleic acid sequence layer without physically contacting the hybridizing reagent layer with the shadow mask.

Because of the improved sensitivity obtained with this invention, no enhancement of signal output with a labeled secondary reagent is required.

The diffraction hybridizing assay method of this invention for determining the presence or quantity of an analyte in an aqueous sample comprises contacting a nucleic acid sequence diffraction biogrid with the sample under proper circumstances and for a sufficient time to permit nucleic acid hybridization between a nucleic acid sequence probe and an analyte; separating the biogrid from the sample; illuminating the biogrid with light from a light source, and determining the light diffracted by the diffraction hybridization assay surface.

The test sample to be assayed can be any medium of interest, and will usually be a liquid sample of medical, veterinary, environmental, nutritional, or industrial significance. Human and animal specimens and body fluids particularly can be assayed by the present method, including urine, blood (serum or plasma), milk, cerebrospinal fluid, sputum, fecal matter, etc. The analyte may pertain to normal, healthy states, or may represent a deviant or diseased state. Where the test sample to be tested contains principally double stranded nucleic acids, such as contained in cells, the sample will be treated to denature the nucleic acids, and if necessary first to release nucleic acids from cells. Denaturation of nucleic acids is preferably accomplished by heating in boiling water or alkali treatment, which, if desired, can simultaneously be used to lyse cells. Also, release of nucleic acids can, for example, be obtained by mechanical disruption (freeze/thaw, abrasion, sonication), physical/chemical disruption (detergents such as TWEEN, TRITON, SDS, alkali treatment, osmotic shock, or heat), or enzymatic lysis (lysozyme, proteinase K, pepsin). The resulting medium will contain nucleic acids in single stranded form which can then be assayed according to the present hybridization method.

DESCRIPTION OF THE DRAWINGS

FIG. 1 is a schematic of incident and diffracted light designs in the method of this invention.

FIG. 2 is a schematic view of a stationary platform embodiment of the diffraction assay apparatus of this invention.

FIG. 3 is a schematic view of a rotating platform embodiment of the diffraction assay apparatus of this invention.

FIG. 4 is a cross-sectional view of a dipstick having mounted thereon, a plurality of insoluble supports with diffraction grating designs of nucleic acid sequence reagents on the surfaces thereof.

FIG. 5 is a fragmentary, magnified cross-sectional view of an insoluble support having nucleic acid sequence hybridizing reagent on the surface thereon in a diffraction grating design.

FIG. 6 is a schematic representation of the process for manufacturing an insoluble support with the diffraction grating design of FIG. 4.

DETAILED DESCRIPTION OF THE INVENTION

This invention is an improvement of an assay applying light diffraction. By forming a grating of hybridized reagent-analyte complexes on the surface of an insoluble support, the incident light can be diffracted into a discrete series of angles, and the light can be detected and measured with a high efficiency. The angle of diffraction is a function of the grating line spacing and the wavelength of the incident light.

The term "analyte" is used herein to designate a substance or substances, either alone or in admixtures, whose presence is to be detected, and, if desired, quantified, The analyte may be a DNA or RNA molecule of small or high molecular weight, a molecular complex including those molecules, or a biological system containing nucleic acids, such as a virus, a cell, or a group of cells. Among the common analytes are nucleic acids, (DNA or RNA) or segments thereof, either single- or double-stranded, viruses, bacteria, cells in culture and the like. Bacteria, either whole or fragments thereof, including both gram positive and gram negative bacteria, fungi, algae and other microorganisms such as Mycoplasmatales, spores, parasites, or yeast are also analytes, as well as animal (e.g., mammalian) and plant cells and tissues. The analyte sample is treated to obtain single-stranded nucleotide sequences which are hybridizable to the nucleic acid sequence of the probe.

The term "probe" refers to nucleotide sequence which is complementary to a nucleotide sequence of a particular analyte and which hybridizes to said analyte nucleotide sequence. The probe may be derived from single or double stranded DNA, RNA, either as a nucleic acid sequence or as nucleic acid sequence contained within a suitable plasmid. Alternatively, the nucleic acid probe may be synthesized by conventional procedures well known in the art. The nucleic acid sequence may be of any appropriate length. Preferred lengths are from 0.1 to 10 Kb, more preferably from 0.2 to 3.0Kb, and especially from 0.5 to 1.0Kb. For hybridization, it is necessary to ensure that the nucleic acid is single-stranded. For double-stranded DNA probes, this is usually achieved by boiling or by denaturing in alkali. The probe is bound to an insoluble support and acts as the primary hybridization reagent.

The term "hybridization assay" or "binding assay" is used herein to designate an assay using any hybridizing reaction between a DNA probe and an analyte which is hybridizable therewith.

The term "light disturbing", as used herein, is defined to include all ways in which light is affected including light absorbing, reflecting, scattering, refracting and phase changing.

The term "diffraction grating design", as used herein, is defined to include a pattern of stripes or lines consisting of active hybridizing agent alternated with inactivated or denatured hybridizing reagent. The active hybridizing agent and inactivated hybridizing agent preferably possess very similar light scattering efficiencies so that the stripes or lines of the diffraction grating design are essentially uniform to light diffraction in the absence of analyte, that is, light is scattered equally strongly from each type of strip before analyte binds preferentially to the active hybridizing agent stripes or lines. The diffraction grating design becomes a diffraction grating with the hybridizing of a light-disturbing analyte.

A "biogrid" or "biograting" refers to a diffraction grating design integrated with a suitable supporting material.

The term "diffraction grating", as used herein, is defined to include reflection amplitude gratings which are formed in one or more steps. In one step gratings, the diffraction grating is formed directly by the binding of the non-light disturbing reagent D on the insoluble surface with an analyte to yield a light disturbing grating pattern. In multistep gratings, the binding product of the reagent on the insoluble surface with the analyte is non-light disturbing, and a second binding with a second binding reagent which is preferably labeled with a moiety which increases the light disturbance. Types of single and multistep gratings formed in the process of this invention include reflection amplitude gratings, transmission amplitude gratings, reflection phase gratings, and transmission phase gratings. In reflection amplitude gratings in one or more steps, light is reflected from the grating, and the amplitude of the reflected light is modulated by the spatially variable reflection of the grating. In transmission amplitude gratings in one or more steps, light is transmitted through the grating, and the amplitude of the transmitted light is modulated by the spatially variable transmission of the grating. In the reflection phase grating in one or more steps, the light is reflected from the grating, and the phase of the reflected light is modulated by the spatially variable refractive index of the grating. In the transmission phase gratings in one or more steps, light is transmitted through the grating, and the phase of the transmitted light is modulated by the spatially variable refractive index of the grating. In the method of this invention, the diffraction grating may function as one or more of these types of gratings concurrently, and all of these grating types are included within the diffraction gratings of this invention.

FIG. 1 is a schematic of incident and diffracted light designs produced by incident light impinging on the diffraction grating in the method of this invention. The incident light 2 impinges on a diffraction grating 4 on the surface of the insoluble support 6. Reflected light 8 (m=0) is reflected at angle $B^0$ which is equal to angle A, the angle of incidence, measured with respect to the normal 10 to the grating surface 4. Diffracted light is diffracted by the grating 4 in a series of angles. The relationship between the angle of incidence and the angle of diffraction is provided by the basic grating equation:

$$m\lambda = d(\sin A - \sin B)$$

wherein m is the spectral order of wavelength $\lambda$, d the groove spacing, and A and B are the angles of incidence and diffraction, respectively, with respect to the normal to the grating surface. The first order diffractions 12 (m=−1) and 14 (m=1) have angles $B^{-1}$ and $B^{+1}$, respectively. The second order diffractions 16 (m=−2) and 18 (m=2) have angles $B^{-2}$ and $B^{+2}$, respectively, with respect to normal 10. Light is also diffracted at higher orders. The first and second order diffractions are shown by way of example, not as a limitation, and all diffractions having a significant intensity can be used in the method of this invention.

FIG. 2 is a schematic view of a stationary platform embodiment of the diffraction assay apparatus of this invention. The light beam 19 from the light source 20 passes through chopper 22 and beam splitter 24. The light passing the splitter passes through collimator 26 and impinges on the diffraction grating 28 mounted on the stationary support 29.

A diffracted beam leaving the grating surface 28 is represented by single line 32 having an angle B with respect to the normal 30. The reflected beam is not shown. The light is collected with lens 4, is passed through an aperture 36 and impinges on the light sensor 38, generating an electrical signal which is carried to the conventional lock-in amplifier and recorder system 40 by cable 42. A split beam 43 of light diverted by the splitter 24 from the primary beam 19 is directed against another light detector 44. The electrical signal from the light detector 44 is fed by cable 46 to the lock-in amplifier 40 as a reference signal for compensating slow drift errors originating from the light source. Cable 48 provides a reference signal from the chopper 22 to the lock-in amplifier 40 for the lock-in function. This function synchronizes the chopper speed (the light bundles passing the chopper) with the operation (opening) of the amplifier filter, thus reducing ambient light noise. The components of the system and their individual functions including the light source, splitter, chopper, collimator, lens, light detectors and lock-in amplifier are conventional and well-known in the art.

The diffraction measuring apparatus schematically represented in FIG. 2 can be constructed to change the angles A and B. The light source 20, chopper 22, beam splitter 24 and collimator 26 can be mounted on an arm which is mounted to rotate in a vertical plane around the diffraction grating 28 to a preferred angle A. Angle A is preferably within the range of from 10 to 80° and optimally within the range of from 20 to 70°. Even more importantly, the lens 34, aperture 36 and light detector 38 can be mounted on an arm for rotation in a vertical plane around the diffraction grating 28 through angles B which place the lens and aperture in the paths of the reflected light beam 8 and the diffracted light beams represented by 12, 14, 16 and 18 in FIG. 1. In this manner, a single detector system can be rotated to detect and measure the reflected light and all desired orders of the diffracted light.

FIG. 3 is a schematic view of a rotating platform embodiment of the diffraction immunoassay apparatus of this invention. The light beam 50 from the light source 52 passes through the beam splitter 54. The light passing the splitter passes through collimator 56 and impinges on the diffraction grating 58 mounted on the rotating support 60.

The diffracted light beam 62 leaving the grating surface 58 has an angle B with respect to the normal 64 to the grating surface. The light is collected with lens 66, is passed through an aperture 68 and impinges on the light sensor 70, generating an electrical signal which is carried to the conventional lock-in amplifier and recorder system 72 by cable 74. A split beam 76 of light diverted by the splitter 54 from the primary beam 50 is directed against another light detector 78. The electrical signal from the light detector 78 is fed by cable 80 to the lock-in amplifier 72 as a reference signal for compensating slow drift errors originating from the light source 52. Cable 81 provides a signal from the platform rotating system 82 to the lock-in amplifier 72 for the lock-in function. This function synchronizes the platform speed (the periodic alignment of the grating and light diffraction designs therefrom with the lens 66 and aperture 68) with the operation (opening) of the amplifier filter, thus reducing ambient light noise. The components of the system and their individual functions including the light source, splitter, light detectors and lock-in amplifier are conventional and well-known in the art.

The diffraction measuring apparatus schematically represented in FIG. 3 can also be constructed to change the angles A and B. The light source 52, beam splitter 54 and collimator 56 can be mounted on an arm which mounted to rotate in a vertical plane around the diffraction grating 58 to a preferred angle A. Angle A is preferably within the range of from 10 to 80° and optimally within the range of from 20 to 70°. Even more importantly, the lens 66, aperture 68 and light detector 70 can be mounted on an arm for rotation in a vertical place around the diffraction grating 58 through angles B which place the lens and aperture in the paths of the reflected light beam 8 and the diffracted light beams represented by 12, 14, 16 and 18 in FIG. 1. As in the embodiment shown in FIG. 2, a single detector system can be rotated to detect and measure the reflected light and all desired orders of the diffracted light.

Alternatively, a stationary array of lens, aperture and detector sets can be positioned at preset angles to coincide with the paths of the reflected and diffracted light for both of the systems of FIG. 2 and FIG. 3. For most simple embodiments of these systems, a stationary lens, aperture and light detector set can be positioned in the path of a first, second or third order diffraction beam. Other suitable combinations of stationary and movable arrays of detectors will be apparent to a person skilled in the art, and all of these permutations and combinations are intended to be within this invention.

The light sources 20 (FIG. 2) and 52 (FIG. 3) are preferably narrow band light sources which can include filtered light from an incandescent light bulb or sunlight. The most preferred light is intense narrow band light which is collimated and optimally polarized. The narrow band frequency can be within the range of from 200 to 1400 nm having a band width within the range of from 10 to 80 nm and is optimally within the range of from 400 to 800 nm having a band width of from 10 to 20 nm or lower. The output power or output energy level of the light source can be 0.1 milliwatts and higher; generally, the higher the power level, the better the results.

The optimum light sources are monochromatic light sources such as lasers. Optimum monochromatic light sources are lasers such as helium-neon laser, diode laser, diode pumped solid state laser, argon ion laser, helium-cadmium laser, YAG, harmonics of YAG, ruby, excimer and tunable dye lasers. The light can be polarized or not polarized. Linear polarization in the plane of incidence is optimum.

The light chopper 22 (FIG. 2) can be any conventional light chopper. It can comprise a rotating plate defining evenly radially spaced windows at a constant distance from the axis of rotation of the plate.

A beam expander can be optionally provided in the light paths 19 and 50 to increase the cross-sectional area of the beams and increase the surface area of the diffraction grating interacting with the light to increase sensitivity. Preferred beam expanders are conventional lens or prism systems which convert an incident collimated light beam into an emitted collimated beam of larger size.

The collecting lenses 34 (FIG. 2) and 66 (FIG. 3) collect each of the diffracted light beams and concentrate or focus them into smaller beams having a cross-sectional area less than the surface area of the light detectors 38 and 70. Any conventional lens system can be used which provides the desired reduction or focusing.

The light detectors 38 and 70 can be any devices which can quantitatively convert incident light intensity to voltage or current in a proportional manner. Conventional light detectors such as photomultiplier tubes or semiconductor-based detectors such as silicon, germanium or gallium arsenide can be used.

The amplifier and recorder systems 40 and 72 can be any conventional system which is customarily used for amplifying an input signal from a light detector and recording a value functionally related thereto. A simple system can comprise a bias supply and an oscilloscope adjusted to show the amplitude of the output signal of each light detector 38 and 70. For more sensitivity, a lock-in amplifier which uses a reference signal from the chopper (FIG. 2) or rotating mount (FIG. 3) to perform the functions described above. These amplifiers are standard, commercially available systems fully within the existing skill of the art and are not a part of this invention.

The platform 6 (FIG. 1) is designed to support a diffraction grating in a precise position of alignment with the incident light beam 2. The configuration of the platform 6 is determined by the shape of the diffraction surface support and whether more than one diffraction surface is mounted on a diffraction surface support.

FIG. 4 is a cross-sectional view of a dipstick having mounted thereon, a plurality of insoluble supports with non-light disturbing diffraction grating designs of reagents on the surfaces thereof. The dipstick body 130 has a plurality of insoluble support surfaces 134 having a diffraction grating design of hybridizing reagent coated thereon. The materials from which the dipstick is made should be nonbinding to minimize non-specific binding during the assay procedure. Suitable dipstick surface materials include polyolefins such as polyethylene and polypropylene, hydrophilic polysilicon and polysiloxane polymers, and the like.

The support for the diffraction grating supports can be any articles upon which the diffraction grating support surface can be mounted. The description of dipsticks are provided by way of example, and not as a limitation. Other articles such as microwells, plates, cavities and the like can be used. For many applications, dipsticks are a preferred embodiment.

FIG. 5 shows one embodiment of a diffraction grating element of this invention. FIG. 5 is a fragmentary, magnified cross-sectional view of an insoluble support having primary hybridizing reagent on the smooth surface thereof in a non-light disturbing diffraction grating design. The insoluble support 140 of this embodiment has a smooth upper surface 142 upon which the diffraction grid design or pattern is coated. The diffraction grating design comprises a plurality of lines 144 of non-light disturbing active primary hybridizing reagent thinly coated and adhering to the upper surface 142. The lines 144 are separated by lines 146 of non-light disturbing deactivated primary hybridizing reagent, for example, primary hybridizing reagent which has been deactivated by exposure to ultraviolet (UV) radiation, other deactivating radiation or other deactivation energy.

The grating can have any number of lines 144 which will provide a diffraction design with the incident light wavelength in the presence of bound analyte. The preferred density of lines 144 are from 250 to 10,000 lines per cm for polarized monochromatic light having a wavelength of from 600 to 800 nm. The optimum density of lines 144 is from 1250 to 2500 lines per cm for polarized monochromatic light having a wavelength of from 600 to 850 nm. The lines 144 have a preferred width (a) of from 0.5 to 20 microns and an optimum width of from 2 to 8 microns. The spacing "d" between the center of adjacent lines 144 is preferably from 0.5 to 20 microns and optimally from 1 to 12 microns. The lines 144 and 146 can be of any desired thickness, depending upon the nature of the primary hybridizing reagent. For nucleic acid sequence coatings adhered to the surface 142 by adsorption or other bonding procedures, the coating thickness is preferably a thin coating, yielding a layer which is non-light disturbing. Prior to the binding of the diffraction grating design with a light disturbing substance, the grating design is non-diffracting, that is, no diffraction occurs when it is exposed to light. When the active primary hybridizing reagent 144 is bound with a light disturbing substance, the grating becomes a diffracting grating. The proportion of light diffracted is a function of the concentration or quantity of light disturbing materials bound with the coating 144, and this value can be used to verify the presence of analyte and to quantify the concentration of analyte present in a sample.

The smooth upper surface 142 of the insoluble support can be any material to which a primary hybridizing reagent can be adhered by physical or chemical bonding and which will not interfere with the reactions which are used to determine the presence and extent of the hybridizing reaction. Organic and inorganic polymers, both natural and synthetic, can be used as the insoluble support. Examples of suitable polymers include polyethylene, polypropylene, polybutylene, poly(4-methylbutylene), butyl rubber, silastic polymers, polyesters, polyamides, cellulose and cellulose derivatives (such as cellulose acetate, nitrocellulose and the like), acrylates, methacrylates, vinyl polymers (such as polyvinyl acetate, polyvinyl chloride, polyvinylidene chloride, polyvinyl fluoride, and the like), polystyrene and styrene graft copolymers, rayon, nylon, polyvinylbutyrate, polyformaldehyde, etc. Other materials which can be used as the insoluble support can be silicon wafers, glass, insoluble protein coatings on a smooth insoluble surface, metals, metalloids, metal oxides, magnetic materials, materials used in semiconductor devices, cermets and the like.

The preferred diagnostic supports of this invention have a superior adsorptive quality for physical, non-covalent binding of nucleic acid sequences, including primary hybridizing reagents and proteinaceous materials applied to reduce the non-specific binding of the ultimate coating. We have discovered that materials previously used in the manufacture of semiconductor devices have superior qualities in this respect. Suitable materials include polished single crystalline silicon, aluminum, epitaxial silicon coatings, silicon nitride coatings, silicon dioxide coatings, and polysilicon coatings. The optimum surfaces have a polysilicon coating. The most optimum supports 140 are single crystal silicon wafers having a polysilicon coating on the outer polished surface thereof.

The polysilicon surface is preferably a thin film of polysilicon deposited on a suitable surface, preferably a highly polished surface such as a single crystalline silicon wafer. Silicon's lattice structure provides a highly uniform surface with superior properties as an reagent support. Polysilicon films were developed in the semiconductor industry as valuable dielectric materials. They are used as gate electrodes in MOS devices, for high value resistors, diffusion sources to form shallow junctions, as conductors and to ensure ohmic contact to crystalline silicon. The term "polysilicon" as used herein is synonymous with the term "polycrystalline silicon" These films are conventionally prepared by chemical vapor deposition techniques. These films and method for their preparation are described by A.C. Adams in "Dielectric and Polysilicon Film Deposition", VLSI TECHNOLOGY. (S.M.Sze ed.) New York: McGraw-Hill, pp 93–129 (1983) and the citations therein, the entire contents of which are hereby incorporated by reference. The surface upon which the polysilicon is coated can be any material which is stable at polysilicon deposition temperatures. It can be prepared by pyrolyzing silane at 600 to 650° C. in a partial vacuum. Lower pyrolysis temperatures are suitable with more reactive silicon sources such as disilane.

The primary hybridizing reagent can be bound to the insoluble support by adsorption, ionic bonding, van der Waals adsorption, electrostatic bonding, or other non-covalent bonding, or it can be bound to the insoluble support by covalent bonding. Procedures for non-covalent bonding are described in U.S. Pat. No. 4,528,267. Procedures for covalently bonding antibodies and antigens to insoluble supports are described by Ichiro Chibata in IMMOBILIZED ENZYMES. Halsted Press: New York (1978) and A. Cuatrecasas, *J. Bio. Chem.* 245:3059 (1970), the entire contents of which are hereby incorporated by reference.

FIG. 6 is a schematic representation of a process for preparing the insoluble support with a diffraction grating design of primary hybridizing reagent shown in FIG. 5. Any smooth surface having the requisite high binding affinity for primary hybridizing reagent can be used in this process. For purposes of clear explanation and not by way of limitation, the process is described for a semiconductor wafer with a polished surface bearing a polysilicon coating. It should be understood that the same, equivalent, or similar procedures can be applied for preparing diffraction gratings designs with primary hybridizing reagents with other high binding smooth surfaces.

With the preferred insoluble supports of aluminum, silicon nitride, silicon dioxide, single crystalline silicon, and in particular the polysilicon surfaces, the primary hybridizing reagent can be applied by simple adsorption. In one procedure for non-covalent adhesion of primary hybridizing reagent to the surface of a insoluble support, a primary hybridizing reagent such as an nucleic acid sequence derived from single or double stranded DNA or RNA, is applied to the surface of a support such as a polysilicon surface 150 in an aqueous buffer solution 152. The buffered primary hybridizing reagent solution is placed in a container with the support bearing the polysilicon surface and incubated at room temperature until adsorption occurs, for example for from 0.5 to 18 hours and preferably from 1 to 3 hours, at temperatures of from 4 to 40° C. and preferably from 20 to 26° C. The polysilicon surface is then rinsed with a buffered saline solution and dried.

The primary hybridizing reagent will comprise at least one single stranded base sequence substantially complementary to or homologous with the sequence to be detected. However, such base sequence need not be a single continuous polynucleotide segment, but can be comprised of two or more individual segments interrupted by nonhomologous sequences. These nonhomologous sequences can be linear, or they can be self-complementary and form hairpin loops. In addition, the homologous region of the probe can be flanked at the 3'- or 5'-termini by nonhomologous sequences, such as those comprising the DNA or RNA of a vector into which the homologous sequence had been inserted for propagation. Such nonhomologous regions are preferably minimized.

Linear or circular single stranded polynucleotides can be used as the probe element, with major or minor portions being duplexed with a complementary polynucleotide strand or strands, provided that the critical homologous segment or segments are in single stranded form and available for hybridization with sample DNA or RNA. Particularly preferred will be linear or circular probes wherein essentially only the homologous probe sequence is in single stranded form.

The concentration of primary hybridizing reagent in the buffer solution is selected to provide the desired reagent density on the polysilicon surface. The primary hybridizing reagent solution can contain from 0.02 to 100 micrograms/ml of the primary hybridizing reagent and preferably contains from 10 to 50 micrograms/ml of the primary hybridizing reagent in a buffered solution having a pH of from 6.0 to 9.5 and preferably from 7.0 to 8.5.

Hybridizing reagent DNA probes are chosen to bind selectively with the analyte to be measured in a sample. Many such sequences have been isolated including DNA sequences for adenoviruses, HCMV, various tumors, normal and aberrant genotypes (e.g., adult or fetal chromosomes), cell products of recombinant DNA processes, bacteria, yeast, algae, etc. In general, the hybridizing reagent is selected to bind specifically or selectively with the analyte, the material for which a sample is assayed.

The hybridizing reagent probes can be derived from natural materials, or can be synthesized by conventional procedures well known in the art and which are not a part of this invention. In general, they can be synthesized by the triester method and the phosphite method, each involving the solid phase method and the liquid phase method. Suitable procedures are described in *Tetrahedron letters*, 1979:3635 (1979), *Nucleic Acids Research*, 8:5473, 5491, 5507 (1980) and *Nucleic Acids Research Symposfum Series*, 7:281 (1980).

The nucleotide probe can be made with a polyadenine, polycytosine, or adenine-cytosine copolymer tail which can be bound to a suitable linking group which facilitates binding of the hybridization reagent to the smooth surface 150.

In an alternate procedure, the linker group can be linked to the pyrimidine base of uridine triphosphate through an allylamine linker arm, and the product can be used as a substrate for probe synthesis using DNA and RNA polymerases in vitro, following a modified procedure of P. Langer, et al., Biochemistry 14 2447-2457 (1975). The 5-(3-amine)allyluridine and deoxyuridine 5'-triphosphates are prepared by reaction with the olefin in the presence of a palladium catalyst.

The surface 150 with the coating 156 of primary hybridizing reagent thereon is then rinsed with deionized water, and dried.

A mask is prepared by photographic methods conventional in semiconductor manufacturing. For example, a mask having a plurality of diffraction grating pattern lines having the desired line density and line widths can be prepared on a quartz glass or other UV-transparent plate through a photoresist process similar to photography. The dark lines of the mask correspond to active primary hybridizing reagent areas desired on the ultimate surface.

In Step C of FIG. 6, the shadow mask 158 is positioned in at a preselected distance from surface 150 to project a precise shadow of lines on the surface 150 having a coating 156 of primary hybridizing reagent thereon using conventional projection alignment techniques. The mercury-xenon illuminator 161 projects an intense, uniform collimated beam of UV light onto a photomask 158. The photomask 158 is mechanically held by a mask holder 159 at the desired distance from the surface 156 to produce non-contact projection of precision images onto the coated surface. The proximity gap 162 can range from 5 to 20 microns from the coated surface 150.

The projection alignment equipment and the projection methods involved in the operation thereof are well known in the art and do not form a part of this invention. The ORIEL TM photolithography illuminator and the accessories therefor (Oriel Corporation, Stratford, CT.) is suitable for this purpose.

In this method, contact of the coating 156 with the mask 158 is entirely avoided, a critical feature which provides the superior diffraction grid of this invention. The surface is exposed to the precisely focused ultraviolet radiation until the hybridizing capability of the portions of the primary hybridizing reagent exposed to the radiation are substantially reduced, or preferably eliminated. To manufacture a precision grating design, the radiation should form a sharp image on the coated surface.

The ultraviolet radiation exposure required to deactivate coating exposed thereto depends upon the primary hybridizing reagent. For nucleic acid sequence reagents, exposure times of from 5 minutes to 60 minutes, and preferably from 10 to 30 minutes is sufficient with a ultraviolet radiation having a wavelength such as 260 nm and a power of from 8 to 20 milliwatts per cm$^2$.

This treatment reduces or eliminates the hybridization properties of the nucleic acid sequence in lines 146, leaving active nucleic acid sequence reagent in a diffraction grating design as the lines 144 of FIG. 5.

The coated substrate containing areas having nucleic acid sequence in a diffraction grating design is then cut into smaller area chips 160, each chip having a size sufficient to perform a nucleic acid sequence hybridization assay. These chips are then mounted on a suitable diagnostic support, such as the dipstick shown in FIG. 4, and are used in hybridization assays.

For most purposes, hybridization can be carried out either in aqueous solution or in the presence of formamide. Formamide is preferred if elevated temperatures will degrade the probe. RNA-DNA RNA-RNA, and DNA-DNA hybridizations can be carried out in formamide, but DNA-DNA hybridizations, only, should be carried out in aqueous solutions. A carrier DNA (denatured DNA, e.g., from calf thymus or salmon sperm) is included in the hybridization solution. Hybridization methods are well known to those skilled in the art, and are detailed in, for example, Maniatis et al. (1982) *Molecular Cloning*, Cold Spring Harbor Laboratory, Cold Spring Harbor, NY, which is hereby incorporated by reference in its entirety.

After hybridization, washing is carried out to remove unhybridized analyte and to dissociate unstable hybrids.

The improved biogrid products of this invention provide improved sensitivity in assay methods using light diffraction. One such method comprises a first step of contacting the insoluble support with the biological diffraction grating design, or pattern of hybridizing agent thereon, with the sample to be assayed for an analyte which hybridizes specifically with the hybridizing agent. The insoluble support is contacted with the sample for a time sufficient to permit binding of the hybridizing agent and the analyte. The sample is then removed from the insoluble support with a suitable buffered rinse solution. This procedure leaves the diffraction grating of hybridizing agent coupled with the analyte.

Light disturbing gratings are directly formed with most analytes. The binding of the hybridizing agent and the analyte converts the hybridizing agent design into a diffraction grating. The nucleic acid sequence of DNA, RNA, or DNA/RNA hybrid, or cell or tissue sample hybridizes and adheres to the insoluble support in a diffraction grating pattern, and light illuminating the surface is diffracted.

If the hybridizing agent-analyte binding product is non-light disturbing, a second step comprises binding the insoluble support with a secondary binding reagent which, in conjunction with the hybridizing agent-analyte binding product, is light disturbing. The secondary binding reagent may be labeled with one or more substances which increase the bound mass, yielding a light-disturbing grid pattern by absorption, reflection, scattering, refraction or phase changing. Specific labels include chromophores and other light absorbing materials, and reflective and light transmitting beads and other light reflecting and scattering materials. Alternatively, the hybridizing agent analyte binding product or the secondary binding reagent can be coupled with a secondary hybridizing reagent which is labeled or which can be specifically bound with a binding partner therefor which is labeled with a chromophore or light absorbing material. This alternative coupling can occur during or subsequent to the secondary binding reagent treatment in the second step. In yet another embodiment, the secondary binding reagent is not itself light-disturbing, but the hybridizing agent-analyte-secondary binding reagent unit acts as a light-disturbing substance.

The choice of secondary binding reagent is made depending upon the type of analyte being assayed. In general, the secondary binding reagent is a nucleic acid sequence coupled to a label. The secondary binding reagent may also be an antibody of a selected class which binds specifically with the analyte, or with the double-stranded hybridization product produced by the hybridization of the primary hybridization reagent and the analyte.

Suitable chromophore labels are any light absorbing pigment or dye which absorbs light of the wavelength produced by the light source. Coupling of the hybridizing reagent-analyte binding product with such a chromophore converts the light diffracting design into a diffraction grating. Alternatively, the light absorbing label can be another type of light disturbing particle or reflective material such as colloidal gold or silver, or latex microspheres.

In the alternative method which has increased sensitivity using the improved biogrids of this invention, the secondary binding partner label binds specifically with a tertiary binding reagent which is labeled with a suitable light disturbing material. Examples of binding pairs for which either partner can be used as the secondary binding partner label are avidin-biotin, IgG antibody-Protein A, hapten-antihapten antibody, and the like. If the secondary binding reagent is an IgG antibody, for example, it can be unlabeled, since the Fc chain portion thereof is a binding partner for Protein A or anti-IgG antibodies.

Following conversion of the biological diffraction design to a diffraction grating, the insoluble support is rinsed with distilled or deionized water. Then the strength of the light diffraction is measured with a suitable light diffraction instrument such as illustrated in FIG. 1. The relative strengths of the light diffracted is a function of the amount of primary hybridizing reagent-analyte conjugate comprising the grating. By repeating the above procedure with a prepared series of solutions containing a range of different known concentrations of analyte therein, a standard curve functionally related to the strength of the diffracted light is obtained. By comparing the reading obtained with the sample containing the analyte with the curve obtained with solutions containing known concentrations of the analyte, the concentration of analyte in the sample can be determined. Comparing the strengths of the first, second, third, etc. order diffractions with each other and with the strength of the reflected light directly provides an indication of the degree of binding with the grating hybridizing agent.

In a competition assay alternative method using the improved biogrids of this invention, the insoluble support with the biological diffraction grating design of hybridizing agent thereon can be contacted with a mixture of the analyte sample and a reagent analyte labeled with a label which is light disturbing. The amount of reagent analyte hybridizing with the primary hybridizing agent will be an inverse function of the amount of analyte in the sample. The density of the diffraction grating formed will therefor have a functional relationship with the concentration of analyte in the sample, and this difference can be detected in the strength of diffracted light.

This invention is further illustrated by the following specific but non-limiting examples. Unless otherwise specified, percents are provided as weight percents and temperature as degrees Centigrade. Examples which have been carried out in the laboratory are set forth in the past tense, and examples setting forth procedures which are constructively reduced to practice herein are set forth in the present tense.

EXAMPLE 1

Single-stranded Probe Preparation

A pBR322 plasmid is treated with Hind III restriction enzyme, and extracted with a mixture of phenol and chloroform to yield the desired pBR322 double-stranded DNA fragment having a molecular weight of 2.0Kb. The pBR322 fragment is dissolved in TRIS buffer (0.01M, pH 8.0) containing 0.001M EDTA, to a final concentration of 0.5 µg/ml. The solution is heated to boiling (100° C.) for five minutes and quickly chilled in an ice bath to produce single-stranded pBR322 DNA.

EXAMPLE 2

DNA Probe coated Wafer

A polysilicon wafer is immersed in the solution from Example 1, containing the single stranded pBR322 DNA. Coating is permitted to proceed inside a refrigerator overnight.

Salmon sperm DNA is dissolved in deionized water, and denatured by boiling at 100° C. for five minutes, then quickly chilled in an ice bath, to yield a carrier DNA solution.

The polysilicon wafer is removed from the coating solution, and immersed in the carrier DNA solution for two hours. The wafer is then removed from the carrier solution, rinsed with deionized water, and dried.

EXAMPLE 3

Diffraction Grating Pattern

A mask having a series of squares corresponding in size and shape to the ultimate biograting product and with diffraction grating lines having a line spacing of ten micrometers, a line width of five micrometers, and a line density of 1000 lines/cm is placed five micrometers away from the single-stranded pBR322 DNA coated wafer produced by the process of Example 1, using a mask alignment fixture. The mask surface is exposed to ultraviolet light having a wavelength of 260 nm for thirty minutes.

The wafer is then cut into square chips having a diffraction pattern of lines of active single-stranded pBR322 DNA thereon, and mounted in a receptive cavity of a dipstick.

EXAMPLE 4

Diffraction Assay for pBR322 Through Hybridization

Double-stranded pBR322 DNA fragments are dissolved in a mixture of SSC (3.0M NaCl, 0.3M trisodium citrate, pH 7.0), formamide (Sigma); Denhardt's solution (1.0% w/v each of polyvinylpyrrolidone-360, Ficoll 500 (Pharmacia Fine Chemicals, Inc.), and bovine serum albumin) 20% Sodium Dodecyl Sulfate, salmon sperm carrier DNA, and deionized water (20:50:10:2.5:2.5:10, v/v). The solution is boiled at 100° C. for five minutes, and quickly chilled in an ice bath. The solution is applied to the dipstick product of Example 2, and incubated at room temperature for two hours. After incubation, the biograting on the dipstick is rinsed thoroughly with distilled water.

The intensity of the light diffracted by the grating is then measured using polarized monochromatic light having a wavelength of 632.8 nm from a helium-neon laser.

EXAMPLE 5

Determination of Salmonella

A sample of Salmonella DNA probe is obtained following the procedures of U.S. Pat. No. 4,689,295, hereby incorporated herein by reference in its entirety. The single-stranded probe is immobilized on a silicon wafer according to the procedure of Examples 2 and 3. Bacterial DNA is then introduced, and hybridization is allowed to proceed for 2 to 3 hours. After incubation, the biograting is rinsed thoroughly with distilled water, and the intensity of the light diffracted by the grating is then measured using polarized monochromatic light having a wavelength of 632.8 nm from a helium-neon laser.

The procedure is repeated with a series of positive controls, each containing a known amount of the salmonella DNA, to establish a reference comparison with which the intensity of the diffracted light obtained with the unknown sample is compared.

EXAMPLE 6

Preparation of HCMV Probe

The EcoRI restriction endonuclease fragment O from human cytomegalovirus (HCMV) strain AD169 (Tamashire et al. J.Virol. p.547–556 (1982), Chou and Merigan NewEng.J.Med. 308:921 (1983)) is cloned into the pBR322 derivative pACYC184 which is used to transfect E. coli strain HB101 Rec A, as described by Tamashire et al. After propagation and purification at the insert-bearing pACYC184, the plasmid is digested with restriction endonuclease EcoRI and the 6.8Kb O fragment of HCMV is purified by preparative electrophoresis in 0.8% agarose gels using standard procedures (Maniatis et al. *Molecular Cloning*, Cold Spring Harbor Laboratory, Cold Spring Harbor, NY. (1982)). The double-stranded O fragment is dissolved in deionized water, and denatured by boiling at 100° C. for five minutes, then quickly chilled in an ice bath to produce single-stranded DNA.

EXAMPLE 7

Detection of HCMV in Urine

A biograting is produced by the methods of Examples 2 and 3, replacing the DNA probe of Example 1 with the HCMV probe of Example 6.

The clinical urine specimen to be tested is prepared in a manner similar to that described by Chou and Merigan (*NewEng.J.Med.* 308:921 (1982)). After clarification of the sample and concentration of the HCMV phage particles by centrifugation, they are resuspended in a minimum volume of 0.5M NaOH and allowed to stand for 15 minutes. After neutralization with a minimum volume of SSC, formamide, Denhardt's solution, 20% SDS, carrier DNA, and deionized water (20:50:10:2.5:2.5:10, v/v), the solution is applied to the dipstick product of Example 2, and incubated at room temperature for two to 3 hours. After incubation, the biograting on the dipstick is rinsed thoroughly with distilled water.

The intensity of the light diffracted by the grating is then measured using polarized monochromatic light having a wavelength of 632.8 nm from a helium-neon laser.

The procedure is repeated with a series of positive controls, each containing a known amount of HCMV sample, to establish a reference comparison with which the intensity of the diffracted light obtained with the patient serum sample is compared.

We claim:

1. A biograting for use in a light diffraction assay comprising a smooth surface having on said surface, a biological diffraction grating design of lines of active hybridizing reagent.

2. The biograting of claim 1 wherein the hybridizing reagent is a nucleotide sequence.

3. The biograting of claim 1 wherein the smooth surface is selected from the group consisting of single crystalline silicon, aluminum, epitaxial silicon coatings, silicon nitride coatings, silicon dioxide coatings, and polysilicon coatings.

4. The biograting of claim 3 wherein the smooth surface is selected from the group consisting of polysilicon and single crystalline silicon surfaces.

5. The biograting of claim 1 wherein the biological diffraction grating design of lines of active hybridizing reagent is substantially non-light disturbing.

6. The biograting of claim 1 wherein the biological diffraction grating design of lines becomes light-disturbing in the presence of hybridization with analyte.

7. A process for manufacturing the biograting of claim 1, comprising adhering a uniform layer of hybridizing reagent on a smooth, solid surface and exposing the surface to UV radiation through a shadow mask with diffraction grating lines to selectively deactivate the hybridizing reagent leaving a biological diffraction grating design of lines of active hybridizing reagent.

8. A process for manufacturing a biograting for use in a light diffraction assay, comprising:
 (a) adhering a uniform layer of hybridizing reagent on a smooth, solid surface; and
 (b) exposing the surface to UV radiation through a shadow mask with diffraction grating lines to selectively deactivate the hybridizing reagent to leave a biological diffraction grating design of lines of active hybridizing reagent.

9. The biograting of claim 8 wherein the hybridizing reagent is a nucleotide sequence.

10. The biograting of claim 8 wherein the smooth surface is selected from the group consisting of single crystalline silicon, aluminum, epitaxial silicon coatings, silicon nitride coatings, silicon dioxide coatings, and polysilicon coatings.

11. The biograting of claim 10 wherein the smooth surface is selected from the group consisting of polysilicon and single crystalline silicon surfaces.

12. The biograting of claim 8 wherein the biological diffraction grating design of lines of active hybridizing reagent is substantially non-light disturbing.

13. The biograting of claim 8 wherein the biological diffraction grating design of lines becomes light-disturbing in the presence of hybridization with analyte.

14. A process for manufacturing the biograting of claim 8, comprising adhering a uniform layer of hybridizing reagent on a smooth, solid surface and exposing the surface to UV radiation through a shadow mask with diffraction grating lines to selectively deactivate the hybridizing reagent leaving a biological diffraction grating design of lines of active hybridizing reagent.

15. An assay method for determining the presence or quantity of an analyte nucleotide sequence in an aqueous sample comprising
 (a) contacting an assay surface with the sample for a time sufficient to permit binding of hybridizing reagent and analyte, the assay surface having on said surface, a light disturbing design of substantially non-light disturbing hybridizing reagent thereon, the hybridizing reagent being selected to hybridize selectively with the analyte; and
 (b) illuminating the assay surface with light from a light source, and determining the light diffracted by the assay surface.

16. The assay method of claim 15 wherein the analyte nucleotide sequence is derived from a body tissue.

17. The assay method of claim 15 wherein the analyte nucleotide sequence is present in a body fluid.

18. The assay method of claim 17 wherein the analyte nucleotide sequence is present in urine, blood serum, blood plasma, milk, cerebrospihal fluid, mucus or sputum.

19. The assay method of claim 17 wherein the analyte nucleotide sequence is present in bacteria, viruses, fungi, algae, animal or plant cells.

20. The assay method of claim 15 wherein the analyte is a nucleotide sequence having origin in a fetal cell, adult cell, bacteria, virus, Mycoplasmatales, spore, algae, parasite, or yeast.

* * * * *

UNITED STATES PATENT AND TRADEMARK OFFICE
CERTIFICATE OF CORRECTION

PATENT NO. : 5,089,387
DATED : February 18, 1992
INVENTOR(S) : Yuh-Geng, et. al.

It is certified that error appears in the above-indentified patent and that said Letters Patent is hereby corrected as shown below:

In column 2, line 39 "in situ" should be in italics.

In column 2, line 40, "in vitro" should be in italics.

In column 5, line 35 delete "D".

In column 18, line 41 delete "cerebrospihal" and insert --cerebrospinal--.

Signed and Sealed this

Twenty-eighth Day of September, 1993

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,089,387
DATED : February 18, 1992
INVENTOR(S) : Yuh-Geng Tsay et al.

It is certified that error appears in the above-indentified patent and that said Letters Patent is hereby corrected as shown below:

Columns 17 and 18, claims 9-13:
Delete "biograting", and substitute therefor
--process--.

Column 18, line 48, claim 20:
Delete "bacteria", and substitute therefor
--bacterium--.

Signed and Sealed this

Eighteenth Day of March, 1997

Attest:

BRUCE LEHMAN

*Attesting Officer*        Commissioner of Patents and Trademarks